US006436420B1

(12) United States Patent
Antelman

(10) Patent No.: US 6,436,420 B1
(45) Date of Patent: Aug. 20, 2002

(54) HIGH PERFORMANCE SILVER (I,III) OXIDE ANTIMICROBIAL TEXTILE ARTICLES

(75) Inventor: Marvin S. Antelman, Rehovot (IL)

(73) Assignee: Marantech Holding, LLC, East Providence, RI (US)

( * ) Notice: Subject to any disclaimer, the term of this patent is extended or adjusted under 35 U.S.C. 154(b) by 0 days.

(21) Appl. No.: 09/477,883

(22) Filed: Jan. 5, 2000

(51) Int. Cl.$^7$ ................................. A01N 25/34
(52) U.S. Cl. .................. 424/404; 424/443; 424/449; 424/402; 424/618; 514/495; 210/758; 210/764
(58) Field of Search ................. 210/758, 764; 424/404, 618, 402, 443, 449; 514/495

(56) References Cited

U.S. PATENT DOCUMENTS

| 2,791,518 | A | | 5/1957 | Stokes et al. ............... 117/120 |
|---|---|---|---|---|
| 4,101,719 | A | * | 7/1978 | Uetani et al. ................ 429/206 |
| 4,410,593 | A | | 10/1983 | Tomibe et al. .............. 428/389 |
| 5,211,855 | A | | 5/1993 | Antelman .................... 210/758 |
| 5,271,952 | A | | 12/1993 | Liang et al. .................... 427/2 |
| 5,336,499 | A | | 8/1994 | Antelman .................... 424/405 |
| 5,458,906 | A | | 10/1995 | Liang ........................ 427/2.31 |
| 5,676,977 | A | * | 10/1997 | Antelman .................... 424/618 |

* cited by examiner

Primary Examiner—Thurman K. Page
Assistant Examiner—Liliana Di Nola-Baron
(74) Attorney, Agent, or Firm—Pennie & Edmonds, LLP

(57) ABSTRACT

Fibrous textile articles possessing enhanced antimicrobial properties are prepared by the deposition or interstitial precipitation of tetrasilver tetroxide ($Ag_4O_4$) crystals within the interstices of fibers, yarns and/or fabrics forming such articles.

19 Claims, No Drawings

HIGH PERFORMANCE SILVER (I,III) OXIDE ANTIMICROBIAL TEXTILE ARTICLES

BACKGROUND OF THE INVENTION

1. Field of the Invention

This invention relates to textile articles possessing antimicrobial properties and a method for their preparation.

2. Description of Related Art

Textile articles which have been treated to render such articles microbicidal to microorganisms coming in contact with the article are known in the prior art. Such articles include those made from paper, fibers, woven and non-woven textiles and like fabrics which are designed for use in environments such as hospitals, food processing plants, laboratories and other areas where maintenance of germ-free conditions is essential.

For example, U.S. Pat. No. 2,791,518 discloses a method of imparting microbicidal properties to articles such as textiles by immersing the article in a first aqueous solution containing a water-soluble basic nitrogen compound (ammonia) and a monovalent silver salt soluble in said solution, followed by a second immersion in a second solution containing a second salt capable of ion exchange with the silver salt such that a monovalent silver salt precipitate is formed within the article. The formed silver precipitate is sparingly water soluble and imparts microbicidal properties to the articles so treated.

Similarly, U.S. Pat. No. 5,271,952 discloses a method of treating fibers to render them electrically conductive as well as anti-bacterial comprising immersing the fibers in a bath comprising an aqueous solution of a source of divalent copper ions, a reducing agent, sodium thiosulfate and a source of iodide ions, whereby copper iodide is adsorbed into the fibers. Similar techniques for rendering fibers conductive or resistant to bacteria involving the use of copper compounds are disclosed in U.S. Pat. Nos. 4,410,593 and 5,458,906.

It has also been disclosed that materials such as chlorinated hydantions may be grafted to textiles for the purpose of imparting antimicrobial properties, ie Williams et al, 218$^{th}$ ACS National Meeting (1999) Abstracts, Cell 32; C&EN September 6, page 36. However, textiles so treated tend to suffer severe diminishment of antimicrobial properties after as few as 5 hours of laundering and are UV unstable over long durations of exposure.

SUMMARY OF THE INVENTION

The invention provides a fibrous textile article containing an antimicrobial agent selected from the group consisting of tetrasilver tetroxide and derivatives thereof interstitially deposited within said article, said agent present in said article in an amount sufficient to impart antimicrobial properties to said article.

The invention also provides a process for imparting antimocrobial properties to a fibrous textile article comprising:

a. providing an aqueous solution containing a water soluble silver salt;
b. contacting said article with said solution for a period of time sufficient to uniformly wet said article with said solution;
c. immersing said wetted article in a bath containing a second aqueous solution containing a strong alkali and a water soluble oxidizing agent and heating said bath for a period of time sufficient to interstitially precipitate tetrasilver tetroxide within said article; and
d. removing said article from said bath.

Textile articles prepared in accordance with this invention, particularly woven and non-woven hydrophilic fabrics, exhibit outstanding antimicrobial resistance with respect to pathogens such as bacteria, viruses, yeast and algae, are resistant to degradation upon exposure to sunlight (ultraviolet light) and maintain their excellent antimicrobial properties even after a number of launderings.

DETAILED DESCRIPTION OF THE INVENTION

Imparting antimicrobial properties to fiber and its derived textile products is achieved in the instant invention by interstitial deposition of the molecular crystal compound tetrasilver tetroxide, i.e., silver (I, III) oxide. Said silver moiety is the subject of several patents. U.S. Pat. No. 5,336,499, the disclosure of which is incorporated herein by reference, describes the anti-pathogenic properties of said silver oxide of formula $Ag_4O_4$ and also the mechanism of operation of the molecular device, based on a unique crystal having two monovalent silver (Ag I) ions and two trivalent silver (Ag III) ions in the molecule. The mechanism of killing pathogens described in the patent is based on the differential silver electronic activity between Ag (I) and Ag (III) resulting in electrocution of pathogens, followed by binding chelation of pathogenic surfaces.

U.S. Pat. No. 5,211,855 also discloses the use of $Ag_4O_4$ crystals to kill pathogens in utilitarian water bodies such as swimming pools.

An antimicrobial spectrum of $Ag_4O_4$ is to be found in a published article written by the instant inventor in the annual R&D issue of *Soap Cosmetics Chemical Specialties* 1994, 70, 3 p. 52–59 entitled "Silver (II, III) Disinfectants", shown in Table 1. The spectrum is based on specifications of the Association of Official Analytical Chemists (AOAC).

TABLE 1

Antimicrobial Spectrum of $Ag_4O_4$

| MICROORGANISM | MIC* (PPM) |
|---|---|
| Gram Negatives | |
| *Escherichia coli* 10231 | 2.50 |
| *Escherichia coli* 25254 | 2.50 |
| *Enterobacter cloacae* 13047 | 2.50 |
| *Pseudomonas aeruginosa* 9027 | 1.25–2.50 |
| Gram Positives | |
| *Bacillus subtilis* 6633 | 5.00 |
| *Micrococcus lutena* 9341 | 1.25–2.50 |
| *Staphylococcus aureus* 0927 | 2.50–5.00 |
| *Staphylococcus aureus* 27543 | 5.00 |
| *Staphylococcus epidermidis* 12228 | 0.625 |
| *Streptococcus agalactiae* 27956 | 1.25–5.00 |
| *Streptococcus faecium* 10541 | 5.00 |
| *Streptococcus-pyogenes* 7958 | 2.50 |
| Yeast and Mold | |
| *Candida albicans* 16404 | 2.50–5.0 |
| *Saccharomyces cerevisiae* 2601 | 1.25 |

*MIC = Miniinal Inhibitory Concentration.

In said article, reference is made to the fact that monovalent silver is more anti-pathogenic than mercury which is more anti-pathogenic than copper, based on their oligodynamic activity as articulated by J. G. Horsfal in his "Principles of Fungicidal Action" (Chronica Botanica 1956). The relative efficacy of metallic moieties against pathogens has been called the Horsfal series, and is as follows:

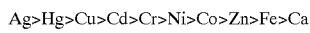

The present inventor has found that with respect to a Horsfal series dedicated to silver, the relative efficacy against pathogens is as follows:

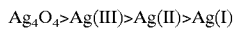

The term "fibrous textile article" as used herein is intended to encompass a wide variety of materials including paper, natural or synthetic fibers, threads and yarns made from materials such as cotton, rayon, wool, jute, nylon, polyesters, polyacetates, polyacrylics as well as cellulosics in general. More particularly, the term refers to fibers woven into a fabric such as knitting, and non-woven hydrophilic fabrics or webbing used in anti-pathogenic applications such as in the medical field, hospitals, biotechnology and food and dairy processing. Exemplary textile products of this genre include bandages, gauze, bandage pads, skin patches, work clothes (both disposable and reusable), bed sheets, masks, dust cloths, safety belts, surgical gowns, ambulance blankets, stretchers, filter materials, diapers, underwear, pajamas, video display terminal screens and the like.

For some antimicrobial applications, $Ag_4O_4$ crystals may be deposited within the interstices of fibrous articles by simply soaking the article in an aqueous dispersion of the crystals or by combining the crystals with a carrier medium and applying this composition to the fibrous article. This method of physical incorporation of the crystals is useful where the article is composed of low density or loosely associated fibers such as bandage pads, gauze pads and loosely non-woven products, and particularly laminated products wherein the treated fibrous article is subsequently sandwiched between one or two peelable layers which tend to keep the crystals trapped in the fibrous article until ready for use. Also, antimicrobial paper products may be made by simply mixing an aqueous dispersion of the $Ag_4O_4$ crystals with paper pulp prior to calendaring the pulp.

However, physical incorporation of the crystals is less effective where the treated article is a fiber or yarn or a higher density woven or non-woven fabric, since the preformed crystals can not sufficiently penetrate into the interstices of such articles. In such cases, deposition of $Ag_4O_4$ material via interstitial precipitation is preferred.

Interstitial precipitation of $Ag_4O_4$ material is accomplished by first providing an aqueous solution of a monovalent water soluble silver salt such as the nitrate perchlorate, acetate, methanesulfonate or fluoride, most preferably silver nitrate. Next the article to be treated, e.g., a fiber, yarn of a woven or non-woven fabric, is thoroughly wetted with this solution such that the article absorbs solution on fiber surfaces as well at one or more of the interstices between fibrils forming the fiber, between fibers forming the yarn or non-woven fabric, or between the weft and woof yarns present in woven fabrics. Wetting may be accomplished by uniformly spraying the article or more preferably by dipping the article in a bath of the silver salt solution for a period of time sufficient for the article to absorb the requisite amount of silver salt solution.

Next the wetted article is optionally squeezed to remove excess solution and immersed in a heated bath containing a second aqueous solution comprising a strong alkali and a water soluble oxidizing agent, and heated for a period of time sufficient to cause reaction leading to the interstitial precipitation of tetrasilver tetroxide ($Ag_4O_4$) crystal material in the interstices of the fibrous article. Suitable alkalis for this purpose include sodium or potassium hydroxide, with sodium hydroxide most preferred. Suitable oxidizing agents include alkali metal persulfates, permanganates or hypochlorites, but sodium and more preferably potassium persulfate is the preferred oxidizer. Reaction in the bath is accomplished by heating at a temperature of at least 85° C., more preferably at least 90° C. for a period of time sufficient to maximize yield of $Ag_4O_4$, generally from about 30 seconds to about 5 minutes. After the reaction is completed, the treated article is removed from the bath and may be washed several times with water to remove soluble inpurities or unreacted reagant.

The quantity of $Ag_4O_4$ material present in the resulting article will generally be a function of the quantity of silver salt sorbed by the article, which can vary depending on the nature of the article, e.g., loose vs. tight weave fabrics or whether the fiber is natural or synthetic, the former being more absorbtive of the silver salt solution.

In general, the quantity of alkali present in the second bath should be sufficient to maintain a strongly basic pH, i.e., about 13+, and providing a slight molar excess of silver salt over oxidizing agent is suitable to complete the reaction. Thus the content of tetrasilver tetroxide interstitially precipitated within any given fibrous article may be controlled by varying the concentration of the silver salt in the solution used to first wet the article and appropriately adjusting the quantities of alkali and oxidizing agent present in the immersion solution at approximately stoichiometric levels.

The term "derivatives of $Ag_4O_4$" is intended to include $Ag_4O_4$ reaction products prepared by reacting $Ag_4O_4$ with suitable water soluble acids to give the corresponding Ag (II) salts, e.g., reactions with fluoroboric acid or phosphoric acid to give the Ag (II) fluoroborate or phosphate, as disclosed in U.S. Pat. No. 5,107,295. Also included are divalent silver nitrate and divalent silver halides prepared by reacting $Ag_4O_4$ with nitric acid or the corresponding haloacids, e.g. HBr, HI or HCl as disclosed in U.S. Pat. No. 5,078,902. Trivalent silver derivatives such as Ag (III) biguanide prepared in accordance with U.S. Pat. No. 5,223, 149 are also included.

Textile articles containing such derivatives would be prepared by further contacting the $Ag_4O_4$ containing article in an additional step with an aqueous solution containing up to stoichiometric amounts of the appropriate reagant(s) sufficient to convert at least a portion of the $Ag_4O_4$ to the Ag (II) or Ag (III) derivative.

Textile articles containing such derivatives are less preferred for the purposes of this invention because some derivatives may be generally more water soluble than $Ag_4O_4$, require a further processing step in their manufacture and are less effective as antimicrobial agents than $Ag_4O_4$ as shown in the silver Horsfal series described above. However, the Ag(II) or Ag(III) derivatives of $Ag_4O_4$ are useful as antimicrobial agents in fabrics which are designed for a single use such as bandages or disposable garments.

The content of the $Ag_4O_4$ or its derivatives (based on weight PPM silver) in the fabric may preferably range from as little as 0.5 weight PPM up to about 50,000 weight PPM, based on the weight of the textile article. The minimum content should be sufficient to kill pathogens from which protection is sought, whereas the maximum content is dictated by factors such as economy and affect on fabric properties. Generally speaking, the higher the silver content, the more effective will be the antimicrobial properties of the fabric. For most applications, silver content in the range of from about 30 to about 10,000 weight PPM will provide satisfactory antimicrobial properties.

Antimicrobial properties are evaluated in accordance with this invention using the Association of Official Analytical Chemists (AOAC) test method 972.04, which is used primarily to evaluate the bacteriostatic activity of laundry additive disinfectants. In this test, a square or rectangular sterile swatch of fabric is pressed into a petri dish containing a layer of nutrient agar which has been inoculated with a pathogen. Following a fixed period of incubation, each fabric sample is evaluated by measuring the clear zones adjacent the four sides of each test swatch as an index of antimicrobial activity. The presence of clear zones along all four sides of the swatch is indicative of antimicrobial activity, rated 4/4. The width of the clear zones in millimeters is reasonably indicative of the degree of antimicrobial activity.

The following examples are illustrative of the invention.

EXAMPLE 1

A swatch of virgin nylon webbing was immersed in an aqueous solution containing dissolved silver nitrate at a concentration of about 100 PPM silver maintained at room temperature. After 30 seconds immersion time, the swatch was removed from this solution and immersed in a hot aqueous solution containing 7.2 g/liter each of NaOH and sodium persulfate, which solution is then boiled for one minute (95–100° C.). The swatch was then removed from the boiling solution, washed with water and dried. There was perceived a hardly visible tan coating on the swatch fibers. The content of $Ag_4O_4$ in the fabric swatch, measured as silver, was 89 weight PPM as verified by gravimetric analysis.

EXAMPLES 2–6

Example 1 was repeated except that the concentration of silver nitrate in the first solution and reagants in the second solution were varied to provide the following Ag content in the fabric swatch:

|      | SOLUTION (PPM Ag) | FABRIC (PPM Ag) |
| ---- | ----------------- | --------------- |
| Ex 2 | 890               | 35*             |
| Ex 3 | 890               | 541             |
| Ex 4 | 10,000            | 3970            |
| Ex 5 | 10,000            | 9140            |
| Ex 6 | 10,000            | 9670            |

*Nylon fabric for this test was of a tighter weave than that used in Example 1 which accounts for the lower silver take up.

AOAC antipathogenic tests on these textiles were performed by an independent laboratory which was licensed by a State environmental regulatory body. The marker organisms used in conformity with AOAC test method 972.04 were Pseudomonas Aeroginosa (PA) as the Gram negative bacteria marker, and Staphylococcus Aureus (SA) for Gram positive bacteria.

The tests were conducted in terms of inhibition of cultures of the bacteria. Two swatches were used for the tests in contact with the cultures. The swatches were 1.5 inches wide and weighed about 69 mg./cm². Each swatch had four sides, and two swatches were used with each representative culture so that a total of eight trials were reflected with each bacterium. An 8/8 inhibition would indicate 100% efficacy. However, the test protocol went beyond the specifications of the AOAC method insofar that the actual average inhibition zone width in millimeters was recorded for both swatches tested. These results were then combined with the aforementioned anti-microbial spectrum shown in Table 1 which includes the marker bacteria of the AOAC tests, and extrapolated. The conclusion was that the preferred embodiments of the invention were 100% effective against all of the microbes shown in Table 1 and against salmonella and the AIDS virus based on the previous independent results obtained with silver (I, III) oxide.

Representative results with nylon fabric are shown in Table 2. Generally, the degree of microbial activity varies directly with the silver concentration. In addition to the high performance anti microbial properties of the fabrics, they withstood wear and could be considered permanent insofar that tested fabrics withstood 100 hours of laundering and 600 hours of ultra violet exposure. Laundering is evaluated using hot water and detergent using the standard test of the American Association of Textile Chemists (AATC).

TABLE 2

Antimicrobial Performance of Precipitated $Ag_4O_4$

| Example Number | Silver PPM | Inhibition Zone-SA (mm) | Inhibition Zone-PA (mm) | Inhibition Index |
| --- | --- | --- | --- | --- |
| 1 | 89   | 3.2 | 1.3 | 8/8 |
| 2 | 35   | 1.8 | 2.0 | 8/8 |
| 3 | 541  | 5.5 | 5.1 | 8/8 |
| 4 | 3970 | 5.8 | 2.6 | 8/8 |
| 5 | 9140 | 5.8 | 2.8 | 8/8 |
| 6 | 9670 | 6.1 | 4.8 | 8/8 |

EXAMPLE 7

An independent medical researcher in Israel obtained a very virulent strain of Staph from a patient at the Shaarei Tzedek Hospital in Jerusalem. The patient subsequently died from infection. This strain was evaluated as more virulent than any of the other Staph microorganisms listed in Table 1 by the pathology staff at the hospital. This Staph strain was utilized as the Staph source, and the otherwise exact test protocol described above was repeated. The silver concentration of the test swatch was found to be 9,138 PPM. Only one test swatch was used for the Staph evaluation. It tested at 4/4 with a much diminished average inhibition zone of 0.50 mm, which was to be expected for the more virulent strain. The values were extrapolated for all Gram positive bacteria listed in Table 1. It was concluded that precipitated $Ag_4O_4$ was capable of inhibiting all of the listed Gram positive bacteria. The extrapolation took into consideration a theoretical calculation of the reduction of the Staph inhibition zone, were the conventional Staph aureus organisms to display the listed MIC range of 2.5–5.0 PPM. Since the inhibition zone is inversely proportional to the MIC, one can calculate that the MIC for the virulent Staph strain was 40.5–61.0 PPM. By applying the same reasoning to the Gram Negative microorganisms for their PA marker, one can claim inhibition as well for all Gram Negative bacteria listed in Table 1 by $Ag_4O_4$.

EXAMPLE 8

The method of Example 1 was repeated with larger amounts of webbing utilizing one-foot lengths. Accordingly, webbing was obtained having respectively 4730 and 9430 PPM of silver. These materials were dyed orange, and the dye completely covered and hid the brown/black color imparted to the virgin webbing by the tetroxide at these relatively high levels. After dyeing, swatches of the webbing were cut from the master rolls and were then evaluated in the same manner as described above by exposure to Staph aureus. All swatches indicated an 8/8 score, with average inhibition zones of 6.3 and 6.0 respectively for the 4730 and 9430 PPM samples. Lengths of the dyed webbing were subjected to 100 hours of laundering in accordance with the AATC method, after which bacteriostatic efficacy was again evaluated. Visual inspection after laundering revealed frayed webbing. Nevertheless, both materials exhibited an 8/8 score with an improvement in inhibition zones to 7.0 for Staph aureus. This indicated that the laundry wear tended to expose fresh surface of tetroxide from the fabric interstices. Swatches were again taken from these materials and exposed to 600 hours of ultra violet light in a weathering test. Evaluations of the UV exposed samples with Staph aureus again indicated scores of 8/8 for both concentrations of silver, with inhibition zones of 6.5 and 4.6, respectively for the 4730 and 9430 PPM silver concentration webbing. Accordingly, ultra violet exposure did not interfere with bacteriostatic activity.

Comparative Example

Monovalent silver iodide was interstitially precipitated within nylon fabric such that the fabric contained 4895 PPM silver. Test swatches were prepared and evaluated against SA and PA pathogens by the test procedure described above. The Inhibition Index for SA was 7/8 and for PA was 0/8. In addition, the SA inhibition zone was only about 0.5 mm.

Fabrics treated in accordance with this invention hold promise for many antimicrobial applications ranging from preventing jock itch when applied to athletic supporters to preventing scabies and bed sores with treated bed sheets or hospital gowns used in nursing homes and hospitals.

What is claimed is:

1. A fibrous textile article containing an antimicrobial agent selected from the group consisting of tetrasilver tetroxide and derivatives thereof interstitially deposited within said article, said agent present in said article in an amount sufficient to impart antimicrobial properties to said article.

2. The article of claim 1 wherein said agent is tetrasilver tetroxide.

3. The article claim 2 wherein said crystals are interstitially deposited by interstitial precipitation.

4. The article of claim 3 wherein said textile article is a woven or non-woven fabric.

5. The article of claim 4 wherein said agent is present within said fabric at a level in the range of about 0.5 to about 50,000 weight PPM, based on the weight of silver.

6. The article of claim 5 containing about 30 to about 10,000 PPM of said agent.

7. The article of claim 3 wherein said antimicrobial properties are sufficient to yield microbial inhibition zones extending beyond 1 mm of fabric swatch borders as measured by AOAC test 972.04.

8. The article of claim 4 wherein said fabric is capable of withstanding at least 100 hours of laundering without significant loss of antimicrobial efficacy.

9. The article of claim 4 wherein said fabric is capable of withstanding at least 600 hours of exposure to ultraviolet light without significant loss of antimicrobial efficacy.

10. A method for producing a textile article having antimicrobial properties, comprising:
    contacting the article with a first solution, the first solution comprising silver; and
    contacting the article with a second solution, the second solution comprising an amount of oxidizing agent sufficient to deposit an antimicrobially active amount of tetrasilver tetroxide within the article.

11. The method of claim 10 wherein said silver comprises silver nitrate.

12. The method of claim 10 wherein said second solution comprises an amount of alkali sufficient to provide a pH of at least about 13.

13. The method of claim 10 wherein said oxidizing agent is potassium persulfate.

14. The method of claim 10 wherein said bath is heated to a temperature in excess of 85° C.

15. The method of claim 10 wherein said article contains from about 0.5 to about 50,000 weight PPM of precipitate, based on the weight of silver.

16. The method of claim 15 wherein said article contains about 30 to about 10,000 PPM of said precipitate.

17. A method for imparting antimicrobial properties to a fibrous article, comprising:
    providing an aqueous dispersion of $Ag_4O_4$ crystals; and
    contacting the article with the aqueous dispersion.

18. The method of claims 17, wherein the article comprises low density or loosely associated fibers.

19. The method of claim 18, wherein the article comprises a bandage, gauze pad, or a laminated product.

* * * * *